(12) United States Patent
Isomae et al.

(10) Patent No.: US 8,625,906 B2
(45) Date of Patent: Jan. 7, 2014

(54) IMAGE CLASSIFICATION STANDARD UPDATE METHOD, PROGRAM, AND IMAGE CLASSIFICATION DEVICE

(75) Inventors: Yuya Isomae, Hitachinaka (JP);
Fumiaki Endo, Hitachinaka (JP);
Tomohiro Funakoshi, Hitachinaka (JP);
Junko Konishi, Hitachinaka (JP);
Tsunehiro Sakai, Mito (JP)

(73) Assignee: Hitachi High-Technologies Corporation, Tokyo (JP)

( * ) Notice: Subject to any disclaimer, the term of this patent is extended or adjusted under 35 U.S.C. 154(b) by 148 days.

(21) Appl. No.: 13/142,812

(22) PCT Filed: Dec. 28, 2009

(86) PCT No.: PCT/JP2009/071774
§ 371 (c)(1),
(2), (4) Date: Jun. 29, 2011

(87) PCT Pub. No.: WO2010/076882
PCT Pub. Date: Jul. 8, 2010

(65) Prior Publication Data
US 2011/0274362 A1 Nov. 10, 2011

(30) Foreign Application Priority Data
Dec. 29, 2008 (JP) ................................ 2008-335779

(51) Int. Cl.
*G06K 9/62* (2006.01)
*G06K 9/54* (2006.01)
(52) U.S. Cl.
USPC .......................................... 382/224; 382/305
(58) Field of Classification Search
USPC ............................ 382/141, 149, 224, 294, 305
See application file for complete search history.

(56) References Cited

U.S. PATENT DOCUMENTS

| | | | |
|---|---|---|---|
| 5,526,258 A * | 6/1996 | Bacus | 382/129 |
| 7,113,628 B1 | 9/2006 | Obara et al. | |
| 7,634,141 B2 * | 12/2009 | Hayashi et al. | 382/224 |
| 8,176,050 B2 * | 5/2012 | Inakoshi et al. | 707/737 |
| 2005/0152592 A1 | 7/2005 | Kasai | |
| 2007/0025611 A1 * | 2/2007 | Kanda et al. | 382/149 |

FOREIGN PATENT DOCUMENTS

| | | |
|---|---|---|
| JP | 08-021803 A | 1/1996 |
| JP | 2001-156135 A | 6/2001 |
| JP | 2005-185560 A | 7/2005 |
| JP | 2005-309535 A | 11/2005 |

OTHER PUBLICATIONS

Written Opinion of the International Searching Authority (PCT/ISA/237) issued in PCT/JP2009/071774 with English Translation dated Mar. 23, 2010.
International Search Report issued in PCT/JP2009/071774 dated Mar. 23, 2010 with English Translation.

* cited by examiner

*Primary Examiner* — Daniel Mariam
(74) *Attorney, Agent, or Firm* — McDermott Will & Emery LLP

(57) ABSTRACT

The objective is to improve a classification standard. Classification standard data, in which is registered image data information that is the standard when image data is classified, and classification data, in which is registered image data information that is the result when newly input image data is classified using the classification standard data, are stored in a storage unit. An image classification device is characterized in that when any image data information of the image data that is registered in the classification data is selected by means of an input unit, and an instruction to additionally register the selected image data information in the classification standard data is input by means of the input unit, the selected image data information is additionally registered in the classification standard data.

18 Claims, 13 Drawing Sheets

FIG.4

121 CLASSIFICATION STANDARD DATA, 122 CLASSIFICATION DATA

| CATEGORY BY USER | CATEGORY BY ADC | DEFECT IMAGE DATA NAME |
|---|---|---|
| C1: PARTICLE | C1: PARTICLE | A1.jpg,A2.jpg,A3.jpg,··· |
| C1: PARTICLE | C2: SCRATCH | — |
| ⋮ | ⋮ | ⋮ |
| C2: SCRATCH | C1: PARTICLE | A10.jpg |
| ⋮ | ⋮ | ⋮ |

FIG.5

124 STANDARD CHARACTERISTIC AMOUNT DATA,
125 CHARACTERISTIC AMOUNT DATA

| DEFECT IMAGE DATA NAME | FLATNESS | BRIGHTNESS | CIRCULARITY | SIZE | ... |
|---|---|---|---|---|---|
| A1.jpg | 50 | 60 | 45 | 55 | ... |
| A2.jpg | 40 | 60 | 30 | 60 | ... |
| ⋮ | ⋮ | ⋮ | ⋮ | ⋮ | ⋱ |

FIG.10

MATRIX

| Manual \ ADC | C1 | C2 | C3 | C4 | C5 | CORRECT RESULT RATIO (%) |
|---|---|---|---|---|---|---|
| C1 | 34 | 1 | 4 | | | 89 |
| C2 | 1 | 15 | | | | 88 |
| C3 | | | 12 | 1 | | 92 |
| C4 | | | | 24 | | 100 |
| C5 | 2 | | 1 | | 8 | 89 |
| PURITY RATIO (%) | 92 | 100 | 71 | 95 | 80 | 90 |

Manual: C1: PARTICLE
ADC: C3: PATTERN SHORT

IMAGE / ANALYSIS

C1: PARTICLE
C2: SCRATCH

| BRIGHTNESS | 95% |
| FLATNESS | 70% |
| CIRCULARITY | 60% |
| SIZE | 45% |
| *** | 15% |
| *** | 5% |

FLATNESS 95% | BRIGHTNESS 70% | CIRCULARITY 60%
SIZE 45% | * 15% | * 5%

SAVE  DELETE

IMAGE CLASSIFICATION STANDARD UPDATE METHOD, PROGRAM, AND IMAGE CLASSIFICATION DEVICE

RELATED APPLICATIONS

This application is the U.S. National Phase under 35 U.S.C. §371 of International Application No. PCT/JP2009/071774, filed on Dec. 28, 2009, which in turn claims the benefit of Japanese Application No. 2008-335779, filed on Dec. 29, 2008, the disclosures of which Applications are incorporated by reference herein.

TECHNICAL FIELD

The present invention relates to a technology of a method and a program for updating an image classification standard, and relates to an image classification device.

BACKGROUND ART

During a process of manufacturing semiconductor products, it is concerned that short circuit may occur on a formed circuit pattern because foreign matter or the like is generated, or a defect such as breaking of wire, and a defect due to a problematic of conditions of a manufacturing process, and the like. In order to improve the product yield ratio, it is necessary to identify the root cause of such a defect at an early stage and to take countermeasures. For this purpose, it is necessary to inspect the semiconductor wafer for foreign matter adhered on a wafer surface and pattern defects formed on the wafer surface by using a device for inspecting foreign matter on semiconductor wafers or a visual inspection device for semiconductor wafers, and thereby continuously monitor occurrence of such defects and take measures to find the causes of such defects, based on inspection results.

Conventionally, such inspection has been carried out visually by a person. Accordingly, classification of detects of observation objects is biased, depending on an inspector. In order to solve this problem, in recent years, technologies for ADR (automatic defect review) and ADC (automatic defect classification), in which a device automatically performs determination of the size, the shape, the kind, and the like of a defect using an image processing technology, have come to be introduced. For example, in order to observe, in another word, review inspected parts (for example, patterns formed on wafers) by using an SEM (scanning electron microscopy) review device, a system that efficiently performs a task while reducing the workload of a user is proposed.

As a method for extracting information included in an inspection image as characteristic amounts and performing automatic classification based on the characteristic amounts, a method using a neural network is disclosed (for example, refer to Patent Document 1). Further, in order to reduce effects of inappropriate characteristic amounts on the classification performance in learning (weighting of respective characteristic amounts) for creating a classification standard for performing automatic classification, a method that automatically selects characteristic amounts that are effective for classification is disclosed (for example, refer to Patent Document 2).

PRIOR ART DOCUMENTS

Patent Documents

Patent Document 1: JP H08-021803 A
Patent Document 2: JP 2005-309535 A

DISCLOSURE OF INVENTION

Technical Problem

In the technology described in Patent Document 1, a classification standard for automatic defect classification using a neural network learns based on visual classification by human eyes. Consequently, if an inspector makes a classification error, there may be a contradiction in the classification standard, resulting in a drop in the classification performance for automatic defect classification. That is, learning is performed via a neural network, based on a classification standard as a result of visual classification, which causes problems that a classification standard with errors is created, and a learning result outputs a result with errors.

Furthermore, in some cases, a desirable classification cannot be performed, since a defect having one type of characteristic may have another type of characteristic if a semiconductor-manufacturing process varies after a currently effective classification standard was created. That is, it is necessary to perform learning each time when a defect of a type that has not been registered in a classification standard is detected.

The technology described in Patent Document 2 does not include a technology for updating a once-created classification standard and thereby improving the classification standard.

The present invention has been developed in view of the foregoing background, and an object of the invention is to improve a classification standard.

Technical Solution

In order to solve the above-described problem, the present invention is a method for updating an image classification standard by using an image classification device for classifying image data, wherein a storage section stores classification standard data in which information on image data to be a standard for classifying image data is registered, and classification data in which information on image data as a result of classification of newly input image data using the classification standard data is registered, and wherein, when information on arbitrary image data is selected via an input section from the image data registered in the classification data, and an instruction is input via the input section to additionally register the selected information on image data into the classification standard data, the image classification device additionally registers the selected information on image data into the classification standard data.

Other solutions will be described later in embodiments.

Advantageous Effects

The present invention can improve a classification standard.

BRIEF DESCRIPTION OF THE DRAWINGS

FIG. 4 is a diagram showing an example of classification standard data and classification data;

FIG. 5 is a diagram showing an example of standard characteristic amount data and characteristic amount data;

FIG. 10 is a diagram showing an example of a self-check screen (characteristic comparison) in the present embodiment;

BEST MODES FOR CARRYING OUT THE INVENTION

Figure 1:
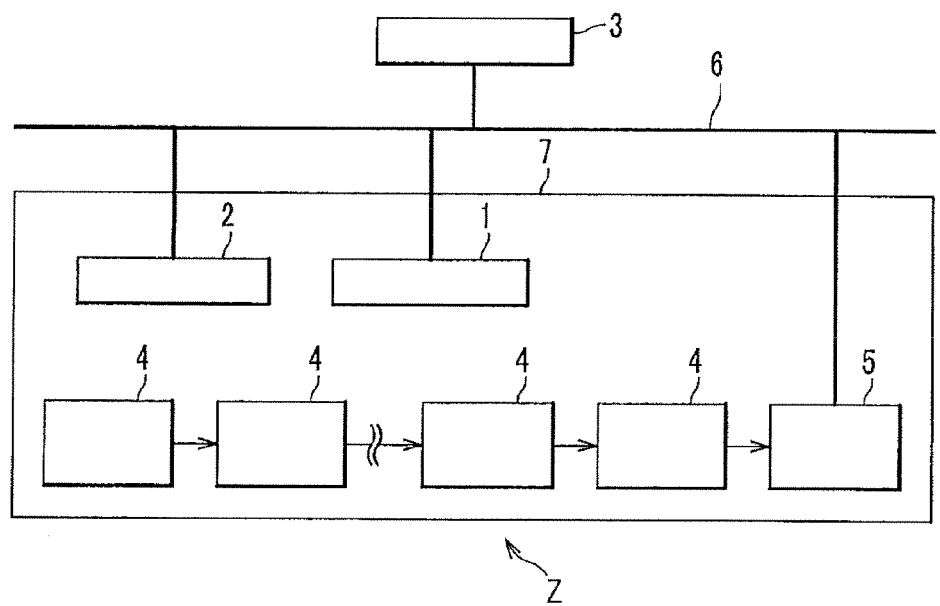
FIG. 1 is a diagram showing an example of the configuration of a semiconductor wafer manufacturing system in the present embodiment.

Modes for carrying out the present invention (referred to as "embodiments") will be described below, referring to the drawings, as appropriate. In the preset embodiment, an example will be described where an image classification device is applied to a semiconductor wafer manufacturing system Z, however, the invention is not limited thereto and is applicable to systems that perform defect inspection using images, such as image inspection of foods.

FIG. 1 is a diagram showing an example of the configuration of a semiconductor wafer manufacturing system in the present embodiment.

Manufacturing devices 4 for manufacturing semiconductor wafers are normally set in a clean room 7 where clean environment is maintained. Further, semiconductor wafers manufactured on the line of the manufacturing devices 4 are subjected to a conduction test by a probe inspection device 5.

In the clean room 7, there are provided appearance inspection devices 2 for detecting appearance defects of produced wafers, and review devices 1 (image classification device) for observation of the appearance defects, in another word, reviewing, based on data from the appearance inspection devices 2. Further, outside the clean room 7, provided is a data processing device 3 that performs processing of image data having been obtained by the appearance inspection devices 2 or the review devices 1. The appearance inspection device 2, the review device 1, the probe inspection device 5, and the data processing device 3 are connected with each other via a communication line 6.

Figure 2:
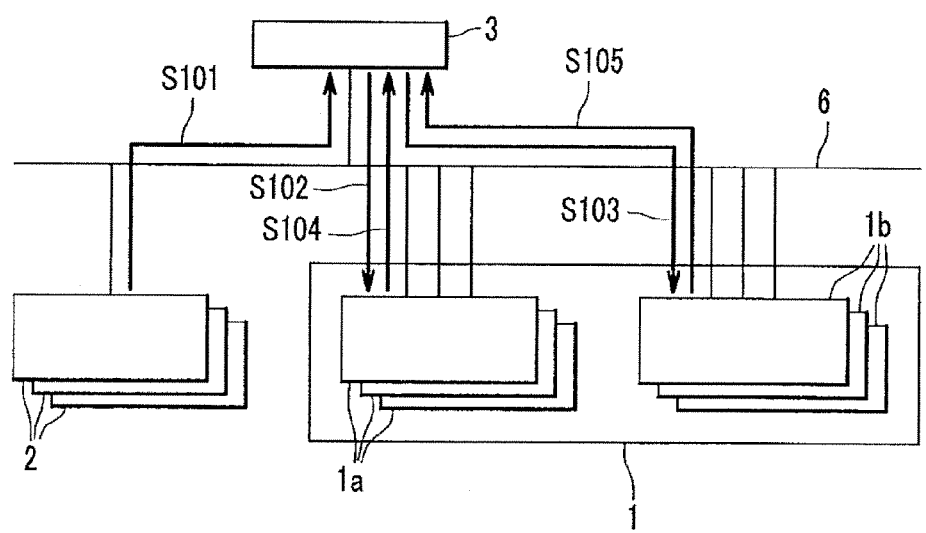
FIG. 2 is a diagram showing the flow of data in a semiconductor wafer manufacturing system in the present embodiment.

FIG. 2 is a diagram showing the flow of data in the semiconductor wafer manufacturing system in the present embodiment. In FIG. 2, elements same as those in FIG. 1 are given with the same symbols, and description will be omitted.

The review device 1 includes a plurality of optical review devices 1a and a plurality of SEM review devices 1b. The optical review devices 1a obtain defect image data, that are data of defect images on semiconductor wafers, obtained by a digital camera connected with an optical microscope, and analyze the defect image data. The SEM review devices 1b obtain defect image data captured by an electronic microscope, and analyze the defect image data. The appearance inspection devices 2, the optical review devices 1a, and the SEM review devices 1b are respectively arranged in plural number, and plural defect image data can be simultaneously obtained.

Semiconductor wafers, which are to become products, flow by lot unit through a plurality of manufacturing devices 4 (FIG. 1). After completion of a process in which appearance inspection of semiconductor wafers is scheduled in advance, a worker or a conveying machine conveys the semiconductor wafers to the appearance inspection device 2, and appearance inspection processing is performed. The appearance inspection device 2 captures the images of the appearance of the semiconductor wafers, and if an appearance defect is detected, the appearance inspection device 2 obtains the coordinates of the position of the detected appearance defect as defect data, and transmits the obtained defect data to the data processing device 3 (S101).

Because the amount of defect data that the appearance inspection device 2 outputs is huge, the data processing device 3 transmits defect data having been filtered by a filter function to an optical review devices 1a or an SEM review devices 1b via the communication line 6 (S102, S103). The filtering function includes, for example, extraction of a predetermined number of pieces of detect information at random.

The optical review devices 1a or the SEM review devices 1b capture the images at the coordinate positions according to the transmitted defect information by using an optical microscope or an electronic microscope, and obtain the images of the semiconductor wafers at the portions of the detected defects (defect image data) of the semiconductor wafers. The optical review devices 1a and the SEM review devices 1b perform classification of defects by using an ADC function implemented therein. Information on results of such defect classification is transmitted as ADR/ADC information via the communication line 6 to the data processing device 3 (S104, S105). In the present embodiment, described is a technology related to a review device 1 (optical review devices 1a, SEM review devices 1b).

Figure 3:
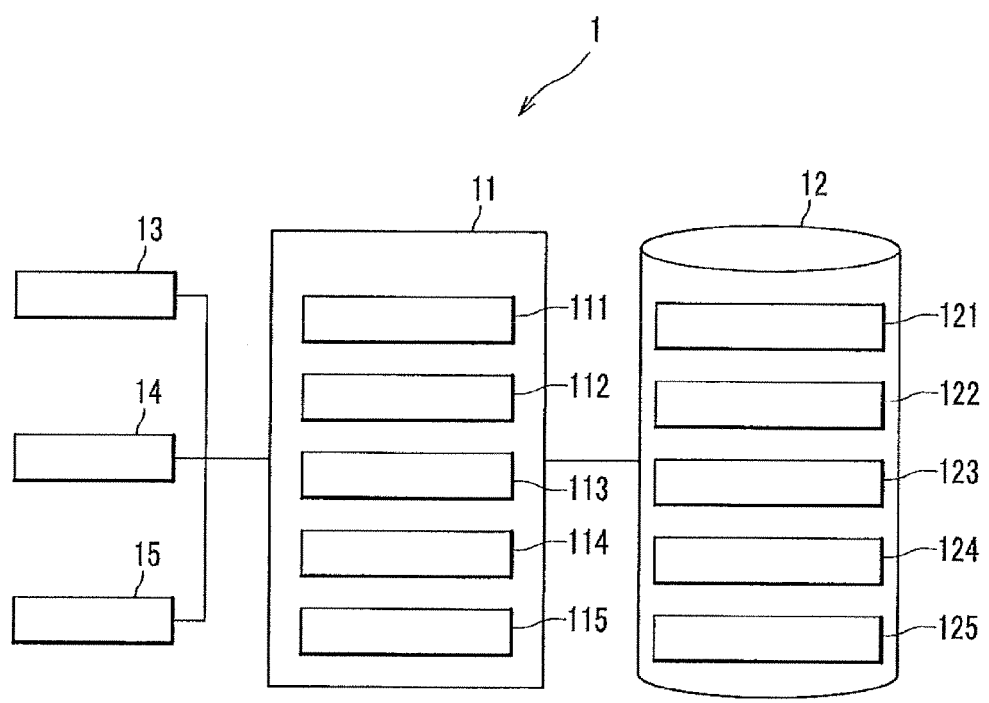
FIG. 3 is a diagram showing an example of the configuration of a review device in the present embodiment.

FIG. 3 is a diagram showing an example of the configuration of a review device in the present embodiment. In the present embodiment, an example is shown where an SEM review device 1b is assumed to be a review device 1, however, the invention is not limited thereto, and may be applied to an optical review device 1a.

A review device 1 includes an input section 13, such as a keyboard or a mouse, a display section 14, such as a display, a transmitting/receiving section 15, such as a communication interface card, a processing section 11 for processing information, and a storage section 12 for storing information.

The processing section 11 includes a display processing section 111, an input processing section 112, an automatic defect classification section 113, a characteristic amount extraction section 114, and a data obtaining section 115. The display processing section 111 has a function of processing information and display the processed information on the display section 14. The input processing section 112 has a function of processing the information having been input from the input section 13. The automatic defect classification section 113 has a function of classifying defect image data by using ADC. The characteristic amount extraction section 114 has a function of extracting the characteristic amounts of respective defect image data. The data obtaining section 115 has a function of obtaining data from the transmitting/receiving section 15.

The processing section 11 and the respective sections 111 to 115 are realized by executing a program stored in a ROM (read only memory), not shown, or a HD (hard disk), not shown, is loaded into a RAM (random access memory), not shown, by a CPU (central processing unit), not shown.

The storage section 12 stores classification standard data 121, classification data 122, a defect image data group 123, standard characteristic amount data 124, and characteristic amount data 125. The classification standard data 121, the classification data 122, the standard characteristic amount data 124, and the characteristic amount data 125 will be described later, referring to FIGS. 4 and 5. The defect image data group 123 are defect image data captured by the review device 1.

Various Data

FIG. 4 is a diagram showing an example of classification standard data and classification data. Herein, the classification standard data 121 are data created by a process, which will be described later with reference to FIG. 6, and the classification data 122 are data created by a process, which will be described later with reference to FIG. 11. Although the classification standard data 121 and the classification data 122 are different in terms of stored data, the formats are similar to each other and will be commonly described below, referring to FIG. 4.

As shown in FIG. 4, the classification standard data 121 and the classification data 122 have a field for categories categorized by user, a field for categories categorized by ADC, and a field for the names of defect image data. The categories by user refer to categories classified by a user in S202 in FIG. 6 (or later-described S403 in FIG. 11). The categories by ADC are those classified by ADC processing in later-described S205 in FIG. 6 (or later-described S401 in FIG. 11). In the example shown in FIG. 4, it is shown that defect image data having been determined to be "C1: particle" by a user and determined to be "C1: particle" also by ADC processing are "A1.jpg, A2.jpg, A3.jpg, . . . ". Further, it is shown that there is no defect image data that has been determined to be "C1: particle" by the user and determined to be "C2: scratch" by ADC processing. Further, it is shown that defect image data that has been determined to be "C2: scratch" by the user and determined to be "C1: particle" by ADC processing is "A10.jpg".

Herein, "C1", "C2", and the like are identification numbers assigned to categories. In the present embodiment, "C1" represents particle, "C2" represents scratch, "C3" represents pattern short, "C4" represents pattern open, and "C5" represents no defect. In the present embodiment, these identification numbers will be used, as appropriate, instead of category names. In addition to these, it is possible to freely set categories, such as to be critical foreign matter, non-critical foreign matter, and false information, without particularly considering image processing or a characteristic amount. That is, the user can freely set category names.

The classification standard data 121 and the classification data 122 may include data related to every possible combination of categories by a user and by ADC, or may include only data related to combinations of categories in which corresponding defect image data actually exists. That is, for example, as shown in line 2 in FIG. 4, records having no corresponding defect image may be omitted. Further, each defect image data may have a format to which information of a category by user and information of a category by ADC are added.

FIG. 5 is a diagram showing an example of standard characteristic amount data and characteristic amount data. Herein, the standard characteristic amount data 124 is data created by a later-described process with reference to FIG. 6, and the characteristic amount data 125 is data created by a later-described process with reference to FIG. 11. Although the standard characteristic amount data 124 and the characteristic amount data 125 are different from each other in terms of data to be stored, their formats are the same; therefore, these data will be explained referring to FIG. 5. As shown in FIG. 5, the standard characteristic amount data 124 and the characteristic amount data 125 each having a defect image data name have characteristic amounts of flatness, brightness, circularity, size, etc.

The process for creating a classification standard will be explained below, based on FIG. 6, referring to FIGS. 3, 4 and 5.

Figure 6:
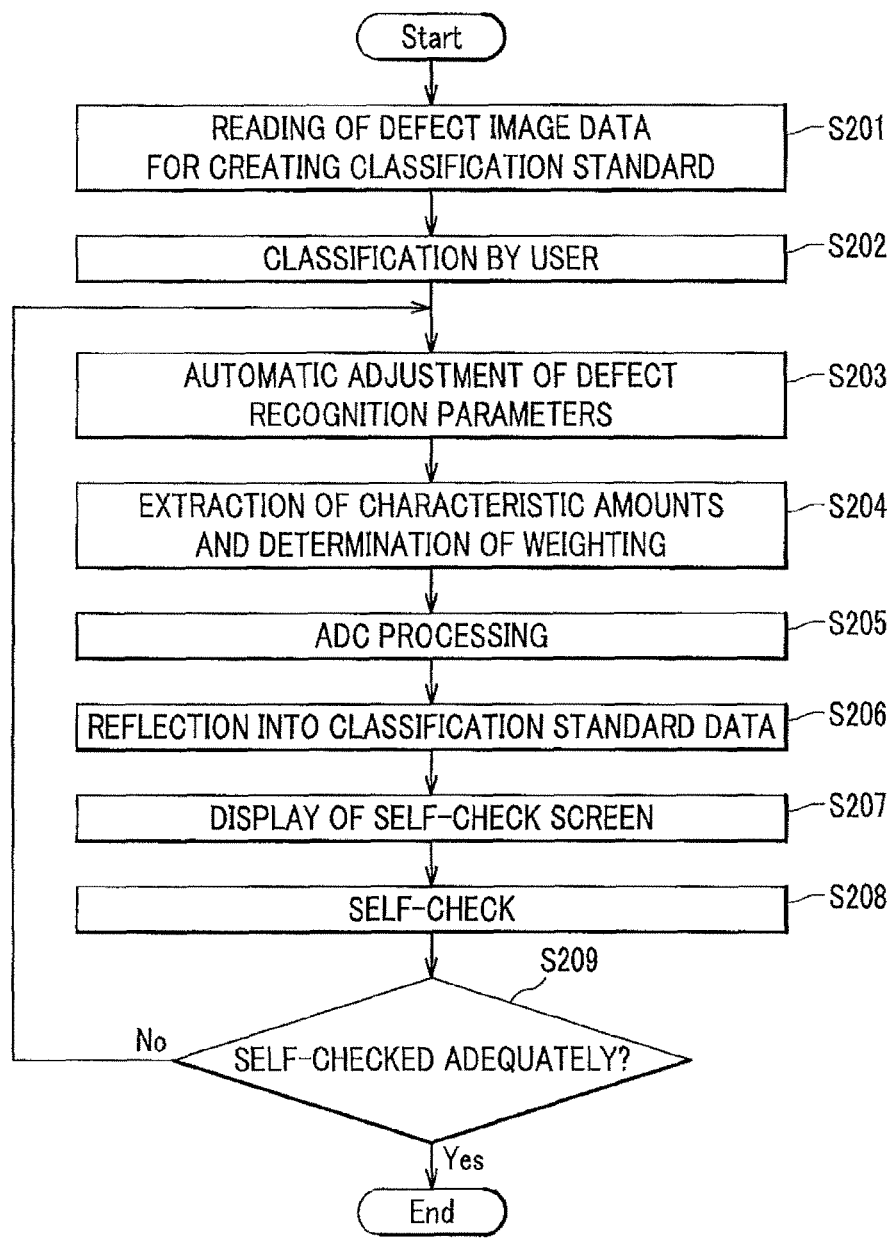
FIG. 6 is a flowchart showing the procedure of a process for creating a classification standard in the present embodiment.

FIG. 6 is a flowchart showing the process for creating a classification standard in the present embodiment. In the process for creating a classification standard as shown in FIG. 6 is a process for creating the classification standard data 121.

First, the processing section 11 reads defect image data for creating a classification standard, from the defect image data group 123 in the storage section 12 (S201).

Then, the user classifies the defect image data obtained via the input section 13 (S202). For example, the user visually classifies the defect image data one by one into kinds, such as particle, scratch, and the like. By the process in S202, initial classification standard data 121 is created.

In the step of S202, only the column of categories by the user is filled in, while the column of categories by ADC is blank.

Subsequent to S202, the characteristic amount extraction section 114 automatically adjusts defect recognition parameters (for example, detection sensitivity, noise removing threshold, protrusion/recession threshold) for extracting characteristic amounts from the defect image data (S203). Herein, the following operation is performed. In recognizing a defect portion and extracting a characteristic amount, the characteristic amount extraction section 114 compares normal image data with defect image data, and then extracts the defect portion. In this state, in order not to erroneously extract a noise on an image as a defect portion, the characteristic amount extraction section 114 removes a noise at a certain level, and in order not to erroneously extract a portion that appears bright due to light as a defect portion, the characteristic amount extraction section 114 adjusts the detection sensitivity. The process in S203 is a technology described in JP 2007-198968 A and others, and accordingly description will be omitted.

Then, after extracting defect potions, the characteristic amount extraction section 114 extracts the characteristic amounts of these defect patterns, and determines how to weight the extracted characteristic amounts when performing ADC (S204). Extracting the characteristic amounts means calculating physical characteristics having been set and quantified in advance for each defect image data. As the physical characteristics, flatness, brightness, circularity, size, as described above, and in addition, height, shape, color, texture, defect, background, and the like can be considered. The characteristic amount extraction section 114 stores the extracted characteristic amounts in the storage section 12 as standard characteristic amount data 124.

Subsequent to S204, the automatic defect classification section 113 performs ADC processing (S205) by using the characteristic amounts extracted in S204 and the determined weight, and classifies the defect image data by ADC. The ADC process is a technology described in JP H09-101970 and the like, and description in detail will be omitted.

Then, the automatic defect classification section 113 reflects a result of the ADC process into the classification standard data 121 (FIG. 4) (S206). The automatic defect classification section 113 registers the result of the classification in S205 into the column, which was blank at the step of S202, as a category by ADC. More specifically, the automatic defect classification section 113 further classifies the classification made at the step of S202 for more details. For example, it will be assumed that "A20.jpg", "A21.jpg", and "A22.jpg", not shown in the drawings, had been determined to be "C3: pattern short" in S202 (classification by the user), however, in S205 (classification by ADC), "A20.jpg" has been determined to be "C1: particle", and "A21.jpg" and "A22.jpg" have been determined to be"C3: pattern short". In this case, "A20.jpg" is classified to be "C3: pattern short" as category determined by the user and to be "C1: particle" as category by ADC, while "A21.jpg" and "A22.jpg" are classified to be "C3: pattern short" as category by the user, and to be "C3: pattern short" as category by ADC.

Incidentally, in case that the classification standard data 121 is not a type as shown in FIG. 4, but a type in which a category names are given to each image data, it is merely required to add the category names as a result of classification in S205 to the corresponding defect image data.

Figure 8:
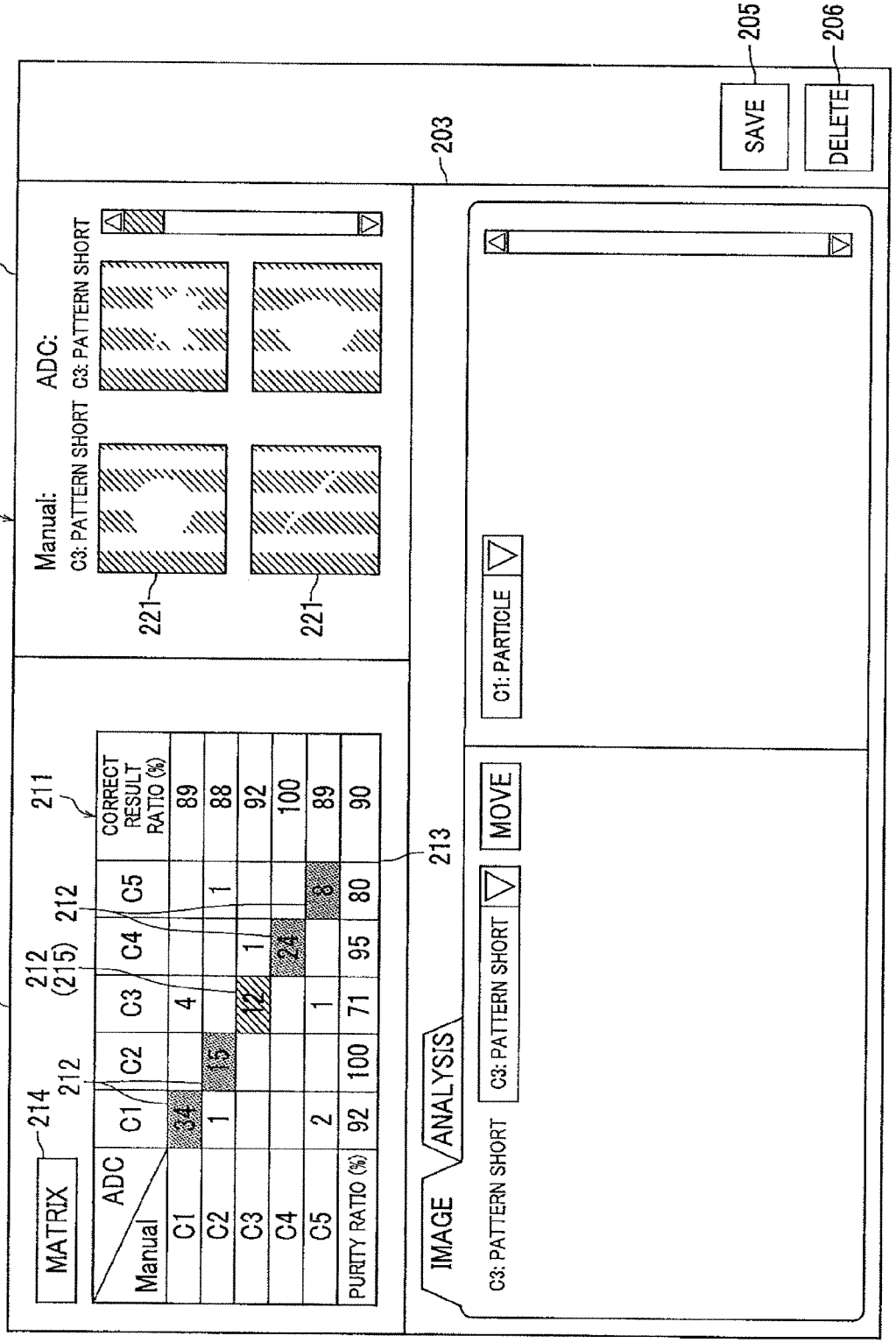
FIG. 8 is a diagram showing an example of a self-check screen (initial screen) in the present embodiment.

Then, the display processing section 111 displays a self-check screen 200, shown in FIG. 8, on the display section 14 (S207), and the user performs self-check via the self-check screen 200 (S208). Self-check will be described later, referring to FIGS. 8 to 10.

Then, from a result of the self-check, the user determines as to whether or not the classification of the classification standard data 121 is adequate (S209).

As a result of S209, if it is determined to be inadequate (determined that the classification of the classification standard data 121 is inappropriate) (S209→No), a change is reflected into the classification standard data 121 and then the process returns to S203 to extract characteristic amounts. Then, the display processing section 111 again performs ADC processing, and displays a result as a self-check screen.

As a result of S209, if it is determined to be adequate (determined that the classification of the classification standard data 121 is appropriate) (S209→Yes), then the process is terminated.

The procedure of a self-check process will be described below, based on FIG. 7 and referring to FIG. 3 and FIGS. 8 to 10.

Figure 7:
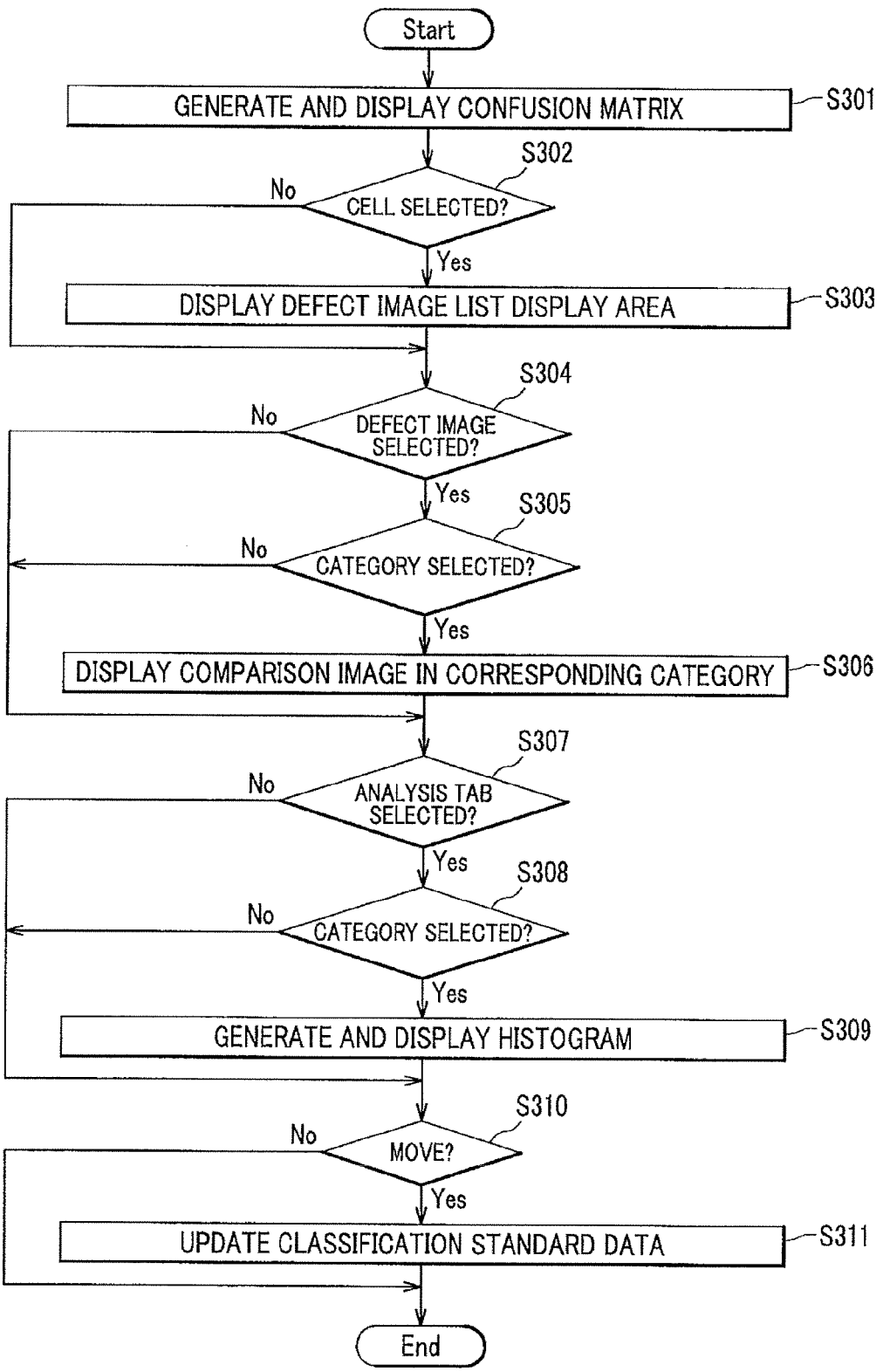
FIG. 7 is a flowchart showing the procedure of a process for self-checking in the present embodiment.

FIG. 7 is a flowchart showing the process for self-checking in the present embodiment.

The process, shown in FIG. 7, is a process corresponding to S207 to S209 in FIG. 6.

First, the display processing section 111 generates a confusion matrix 211 (association information between categories), and displays a self-check screen 200*a* (FIG. 8) including the generated confusion matrix 211 (S301).

FIG. 8 is a diagram showing an example of a self-check screen (initial screen) in the present embodiment.

The self-check screen 200*a* (200) includes a confusion matrix display area 201, a defect image list display area 202, and a defect image confirmation area 203, which are displayed in the same window.

In the confusion matrix display area 201, a confusion matrix 211 is displayed. The confusion matrix 211 is a table that indicates the numbers of images in the respective categories according to the classification by the user (represented by "Manual" in FIG. 8), and the respective categories according to the classification by ADC (represented by "ADC" in FIG. 8).

Symbols C1 to C5 are, as described above, category identification numbers, wherein "C1" represents particle, "C2" represents scratch, "C3" represents pattern short, "C4" represents pattern open, and "C5" represents no defect.

In the example in FIG. 8, the vertical axis represents categories according to classification by the user ("Manual"), and the horizontal axis represents categories according to classification by ADC.

For example, regarding line 1 of the confusion matrix 211, 38 (34+4) defect image data are determined to be C1 (particle) according to the classification ("Manual") by the user, while 34 defect image data among them are determined to be C1 (particle) and 4 defect image data among them are determined to be C3 (pattern short) according to the classification by ADC. A correct result ratio is the ratio of a classification result by ADC that agrees with a classification result by user, to the classification result by the user. For example, the correct result ratio of line 1 is 34/38×100≅89 (%).

Likewise, regarding row 1 in the confusion matrix 211 in FIG. 8, it is recognized that 37 (34+1+2) defect image data are determined to be C1 (particle) by ADC, while one defect image data is determined to be C2 (scratch) and two defect image data are determined to be C5 (no defect) by the user. A purity ratio is the agreement ratio of a result of classification by user to a result of classification by ADC. For example, the purity ratio of row 1 is 34/37×100≅92 (%).

The elements having a reference symbol 212 (the central oblique line) in the confusion matrix 211 represent the numbers of defect image data in which classification by user conforms with classification by ADC for the respective categories. Further, symbol 213 represents the ratio of the number of defect image data, in which classification by user conforms with classification by ADC, to the total number of all defect image data.

When a matrix button 214 in the input section 13 is selected and entered, the display processing section 111 counts the numbers of defect image data in the respective categories, referring to the classification standard data 121, shown in FIG. 4, and displays the counted numbers in the confusion matrix 211.

Herein, the display processing section 111 monitors whether or not a cell of the confusion matrix 211 has been selected (S302 in FIG. 7).

Figure 12:
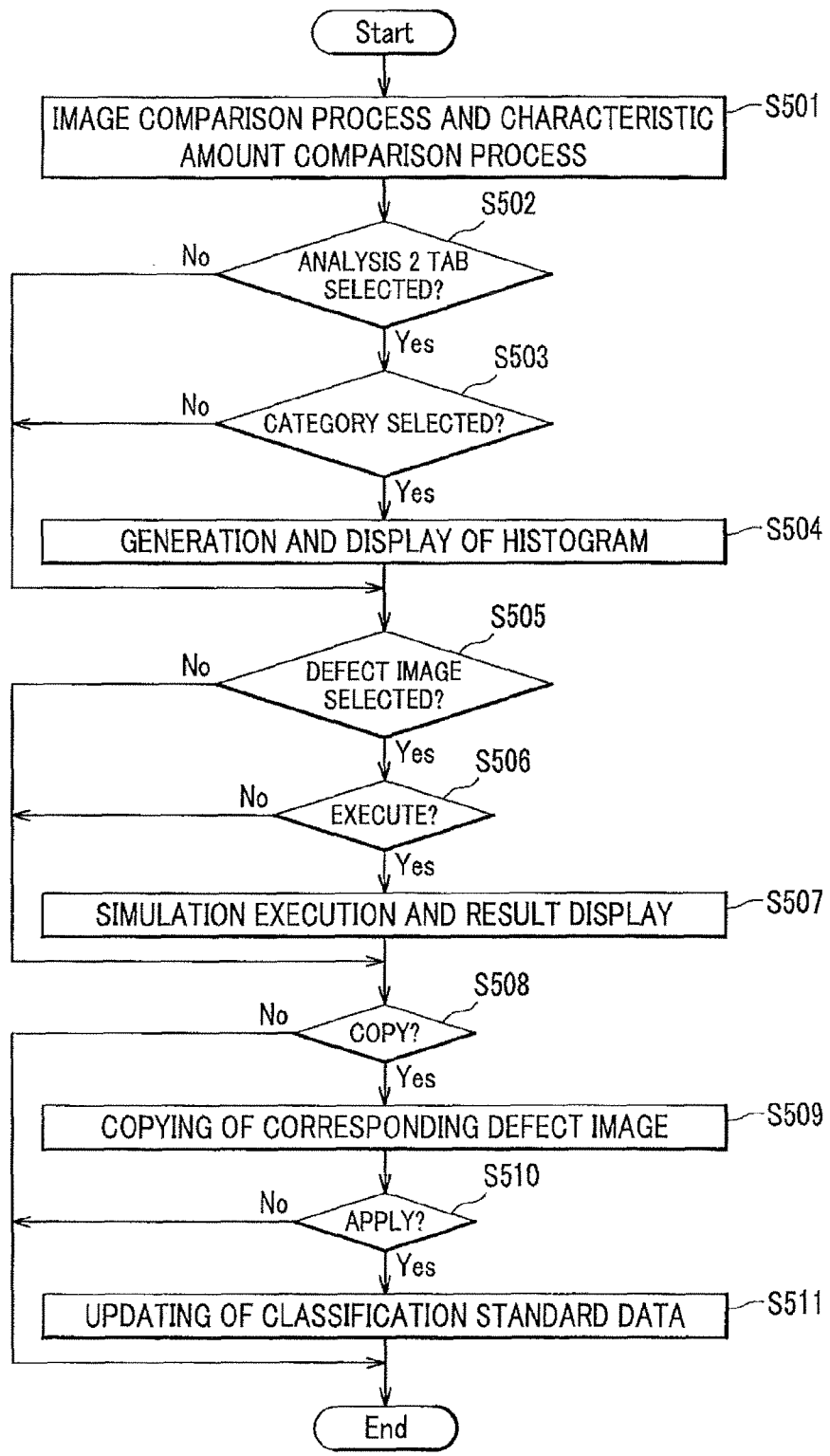
FIG. 12 is a flowchart showing the procedure of a check process in the present embodiment.

When no cell is selected (S302→No), the display processing section 111 forwards the process to S304. In FIG. 7 and in FIG. 12, if the process moves forward to the step No. Sm when no selection input is made in step No. Sn, it means that the processing section 11 determines nothing and executes the process of the step Sm. This is because, the steps in FIG. 7 and FIG. 12 are actually image processing steps, and each step is executed when an instruction is input, regardless of the order of the steps shown in the drawings.

If the user selects one of the cells in the confusion matrix 211 (S302→Yes, in FIG. 7), then a defect image corresponding to the selected cell is displayed in the defect image list display area 202 (S303 in FIG. 7).

For example, if a cell 215, whose category is C3 (pattern short) according to classification by user ("Manual") and is also C3 (pattern short) according to Classification by ADC, is selected and entered via the input section 13, then the display processing section 111 obtains, from the classification standard data 121 in FIG. 4, the names of defect image data stored in the records of both categories by the user and ADC "C3: pattern short". Then, the display processing section 111 obtains, from the defect image data group 123 (FIG. 3) in the storage section 12, image data corresponding to the obtained name of defect image data, and displays the obtained image data in the defect image list display area 202.

Incidentally, in FIG. 8, as "12" is described in cell 215, the number of images displayed in the defect image list display area 202 is also 12. The user can refer to 12 images by moving the slide bar in the defect image list display area 202 shown in FIG. 8.

In the defect image confirmation area 203, nothing is displayed at the step of S303. A save button 205 and a delete button 206 will be described later.

In order to create accurate classification standard data 121 and thereby improve the accuracy of classification by ADC, it is necessary to improve the purity ratio and the correct result ratio in the confusion matrix 211.

A method for updating the classification standard data 121 for improving the purity ratio and the correct result ratio will be described below, referring to FIGS. 9 and 10. Incidentally, in FIGS. 9 and 10, elements that are similar to those in FIG. 8 are given with the same symbols, and description will be omitted.

Figure 9:
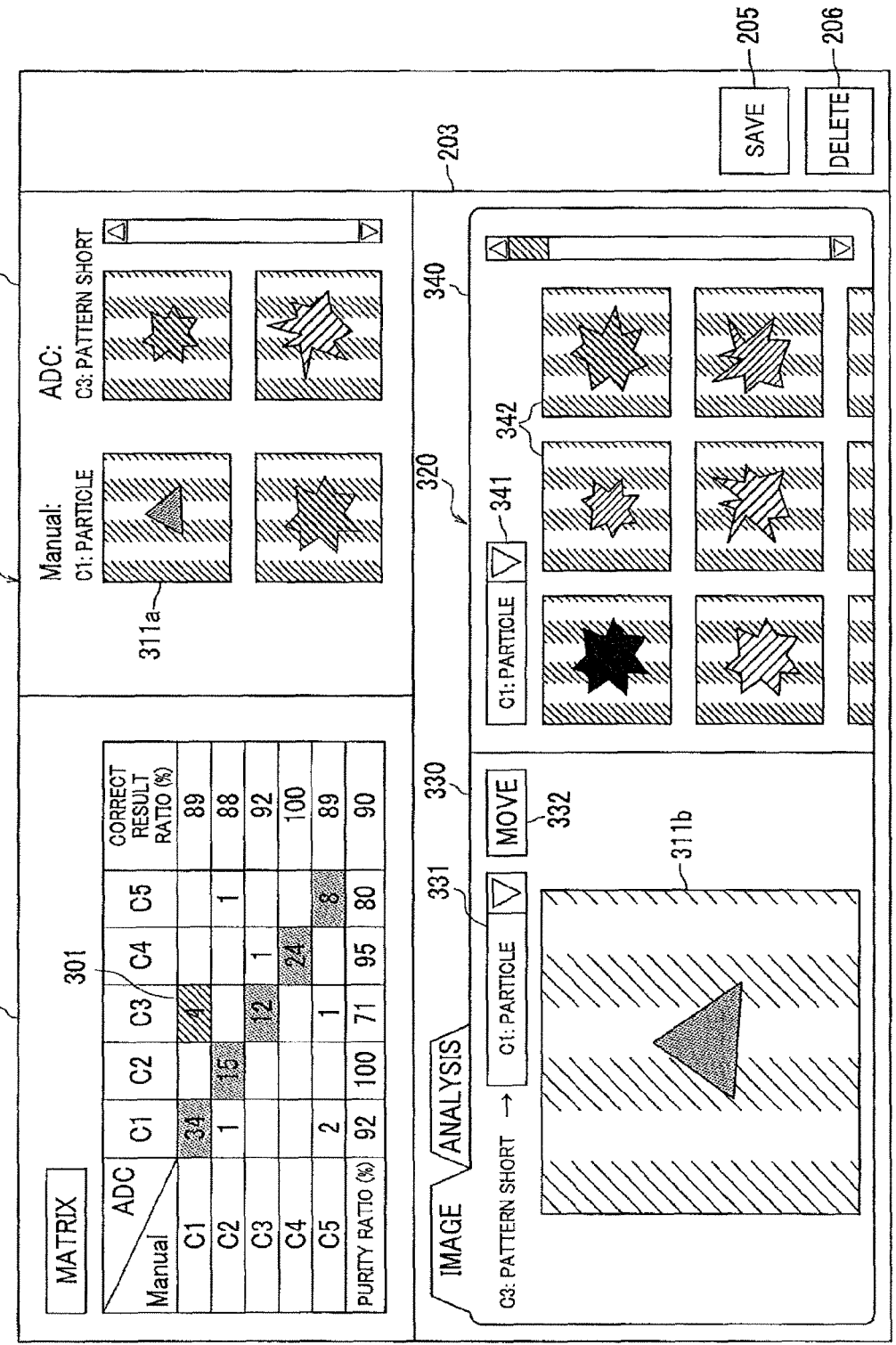
FIG. 9 is a diagram showing an example of a self-check screen (image comparison) in the present embodiment.

FIG. 9 is a diagram showing an example of a self-check screen (image comparison) according to the present embodiment.

In FIG. 9, an example is shown where, in the confusion matrix 211, a cell 301 whose classification by user ("Manual") is "C1: particle" and whose classification by ADC ("ADC") is "C3: pattern short" is selectively input.

The display processing section 111 determines whether or not a defect image displayed in the defect image list display area 202 has been selected (S304 in FIG. 7). If no defect image has been selected (S304→No), then the display processing section 111 proceeds the process to S307 in FIG. 7.

If the user drags and drops a defect image 311a from defect images displayed in the defect image list display area 202 to the defect image confirmation area 203 (S304→Yes, in FIG. 7), then the dragged and dropped defect image 311a is copied to an object image display area 330 in a image comparison area 320 in the defect image confirmation area 203, and enlarged and displayed as a defect image 311b.

Further, in a comparison image display area 340, defect images 342, which belong to a category selected via a category selection pull-down menu 341, are displayed. A category which is selected via the category selection pull-down-menu 341 is a category according to classification by user. If the user wishes to compare images in a category with images in another category, the user selects said another category by using the category selection pull-down-menu 341 via the input section 13.

More specifically, the display processing section 111 determines whether or not a category has been selected by the category selection pull-down-menu 341 (S305 in FIG. 7). If no category has been selected (S305→No), then the display processing section 111 proceeds the process to S307.

If a category is selected by the category selection pull-down-menu 341 (S305→Yes, in FIG. 7), then the display processing section 111 refers to the classification standard data 121 in FIG. 4, with a key of the selected category, and thereby obtains the names of defect image data stored in all records corresponding to the selected category with classification by user. Then, the display processing section 111 obtains defect image data corresponding to the obtained names of defect image data from the defect image data group 123 (FIG. 3) in the storage section 12, and displays the obtained defect image data in the comparison image display area 340 as comparison images in the corresponding category (S306 in FIG. 7).

A characteristic amount display area 400 (FIG. 10) is hidden at the back of the image comparison area 320, and the characteristic amount display area 400 (FIG. 10) is displayed in front by selectively inputting "analysis tab" via the input section 13.

That is, the display processing section 111 determines whether or not "analysis tab" has been selectively input (selected) (S307 in FIG. 7), and if the analysis tab has not been selected (S307→No), the display processing section 111 proceeds the process to S310 in FIG. 7.

If the analysis tab has been selected (S307→Yes), then the display processing section 111 displays the characteristic amount display area 400 shown in FIG. 10.

FIG. 10 is a diagram showing an example of a self-check screen (for comparing characteristic amounts) according to the present embodiment.

If the user drags and drops an arbitrary defect image 401a displayed in the defect image list display area 202 on the self-check screen 200c (200), to the characteristic amount display area 400, then the dragged and dropped defect image 401a is copied and displayed in the characteristic amount display area 400 as a defect image 401b.

The display processing section 111 determines whether or not a category whose characteristic amounts the user intends to display has been selected via a characteristic amount selection pull-down-menu 402, 403 (S308 in FIG. 7), and if not selected (S308→No), the display processing section 111 proceeds the process to S310 in FIG. 7.

If a category whose characteristic amounts the user intends to display has been selected via the characteristic amount selection pull-down-menu 402, 403 (S308→Yes, in FIG. 7), then the display processing section 111 generates a histogram representing the distribution of the respective characteristic amounts in the selected category, and displays the generated histogram in a characteristic amount distribution display area 411 (S309 in FIG. 7). A category selected via the characteristic amount selection pull-down-menu 402, 403 is a category classified by user.

In graphs displayed in the characteristic amount distribution display area 411, the horizontal axis represents the values of respective characteristic amounts and the vertical axis represents the numbers of defect image data with the respective values. In the characteristic amount distribution display area 411, the characteristic amount distribution of a category selected via the characteristic amount selection pull-down-menu 402 is displayed as a hollow histogram, and the characteristic amount distribution of a category selected via the characteristic amount selection pull-down-menu 403 is displayed as a hatched histogram. Further, a portion where the characteristic amount distribution of a category selected via the characteristic amount selection pull-down-menu 402 and the characteristic amount distribution of a category selected via the characteristic amount selection pull-down-menu 403 overlap with each other is displayed as a black solid histogram. In the example, shown in FIG. 10, the characteristic amount distribution of "C1: particle" is displayed by a hollow histogram, and the characteristic amount distribution of "C2: scratch" is displayed by a hatched histogram. The percentage displayed in the right top portion of a characteristic amount distribution display area 411 represents the separation degree that is the ratio of the non-overlapped distribution portion to the entire characteristic distribution in two categories. That is, the percentage represents the ratio of the histograms which are not black-solid to the entire characteristic amount distribution. It is shown that if the separation degree is larger, the difference is the greater between the characteristic amount distributions of two categories.

A histogram representing characteristic amount distribution is created in the following procedure. First, the display processing section 111 searches a category by the user in the classification standard data 121 in FIG. 4 by using the category name selected via the characteristic amount selection pull-down-menu 402 as a key, and obtains the names of defect image data included in all corresponding records.

Then, the display processing section 111 searches in the standard characteristic amount data 124 in FIG. 5 by using the obtained defect image data names as a key, refers to the values of the respective characteristic amounts corresponding to the defect image data names, and counts the number of defect image data with the same characteristic amount on each individual characteristic. For example, in the example in FIG. 5, assuming that "A1.jpg" and "A2.jpg" are objects of processing, the display processing section 111 first refers to record "A1.jpg" and counts "flatness: 50" by +1, and counts "brightness: 60" by +1. The display processing section 111 likewise counts "circularity" and "size" of this record as well.

Then, the display processing section 111 refers to record "A2.jpg", and counts "flatness: 40" by +1, and counts "brightness: 60" by +1 ("brightness: 60" thereby becomes "2"). The display processing section 111 likewise counts "circularity" and "size" of this record as well.

The display processing section 111 performs this process on all the obtained names of defect image data, thereafter further performs the same process also on the category selected via the characteristic amount selection pull-down-menu 403, and calculates the histograms of characteristic amounts for the respective characteristics.

Further, bars 412 in the characteristic amount distribution display area 411 represent the respective values of the characteristic amounts of the defect image 401b. The display processing section 111 obtains the values of characteristic amounts from the standard characteristic amount data 124 in FIG. 5, by using the name of the defect image data of the defect image 401b as a key, and displays bars 412 at positions representing the respective characteristic amounts corresponding to the values obtained by the display processing section 111.

In a separation degree list display area 431, the above-described separation degrees are listed in the descending order.

Radio buttons 421, 422 are used to indicate characteristic amounts which are currently used in performing classification by ADC processing. In the example in FIG. 10, "flatness", "brightness", and "circularity", for which the radio buttons 421, 422 are "ON", are characteristic amounts which are currently used in the ADC process. By switching "On/Off" of the radio buttons 421, 422, the user can set effectiveness/ineffectiveness of characteristic amounts to be used in the ADC process. For example, when the user determines that "brightness" and "circularity" are ineffective characteristic amounts, the user can set the usage of these characteristic amounts in the ADC process to be ineffective by selecting and entering the corresponding radio buttons 412, 422. Further, on the contrary, when the user determines that "size" is valid characteristic amount, the user can set the usage of this characteristic amount in the ADC process to be effective by selecting and entering the corresponding radio buttons 421, 422.

By determining whether or not a move button 332 (FIG. 9) has been selected and entered, the display processing section 111 determines whether or not to move corresponding defect image data from the current category to another category (S310 in FIG. 7), and if not to move (S310→No), the processing section 11 terminates the process. Herein, "not to move" refers to a case, for example, where a delete button 206 is selected and entered, or the user closes the self-check screen 200 in a state that the move button 332 has not been selected and entered. Incidentally, S310 corresponds to the process in S209 in FIG. 6.

If the user intends to move the current defect image from the current category to another category, the user selects a moving destination category via a moving-destination-category selection pull-down menu 331 and selects and enters the move button 332 (FIG. 9) (S310→Yes, in FIG. 7), and thereupon the display processing section 111 moves the data name of the defect image 311b displayed in the object image display area 330 (FIG. 9) to the selected moving destination category. More specifically, the display processing section 111 moves the name of the defect image data corresponding to the defect image 311b to a record of the selected moving destination category selected by the user in the classification standard data 121, and thereby updates the classification standard data 121 (S311 in FIG. 7).

Further, if a defect image displayed in the object image display area 330 is an inappropriate (for example, a case where the image of a defect is not correctly captured) image for creating the classification standard data 121, then the delete button 206 is selected and entered via the input section 13, and thereupon, the display processing section 111 can delete the name of this defect image data from the classification standard data 121.

When the user has moved a defect image data name to be used for learning to another category by selecting and entering the move button 332 (FIG. 9), when the user has deleted defect image data from the classification standard data 121 by selecting and entering the delete button 206, or when the user has switched effectiveness/ineffectiveness of a characteristic amount to be used for ADC processing, it is possible to update the confusion matrix 211 by selecting and entering the matrix button 214 each time. Further, the classification standard data 121 in this state can be overwritten or saved with another name by selecting and entering the save button 205.

The classification standard data 121 having been created in such a manner is used as a classification standard for ADC processing in the review device 1, and the review device 1 automatically classifies defects on semiconductor wafers and transfers identification numbers of categories in respective results to the data processing device 3. On the other hand, the defect image data group 123 determined to be defect images by ADC is stored in the storage section 12 of the review device 1 for respective wafers.

Through the process up to here, a classification standard data 121 has been created and adjusted for classification of defect images by ADC. A process to be performed when new defect image data is transmitted to the review device 1 after the classification standard data 121 is created will be described below, referring to FIGS. 10 to 14. The transmitted new defect image data is stored in the defect image data group 123 in the storage section 12.

Figure 11:
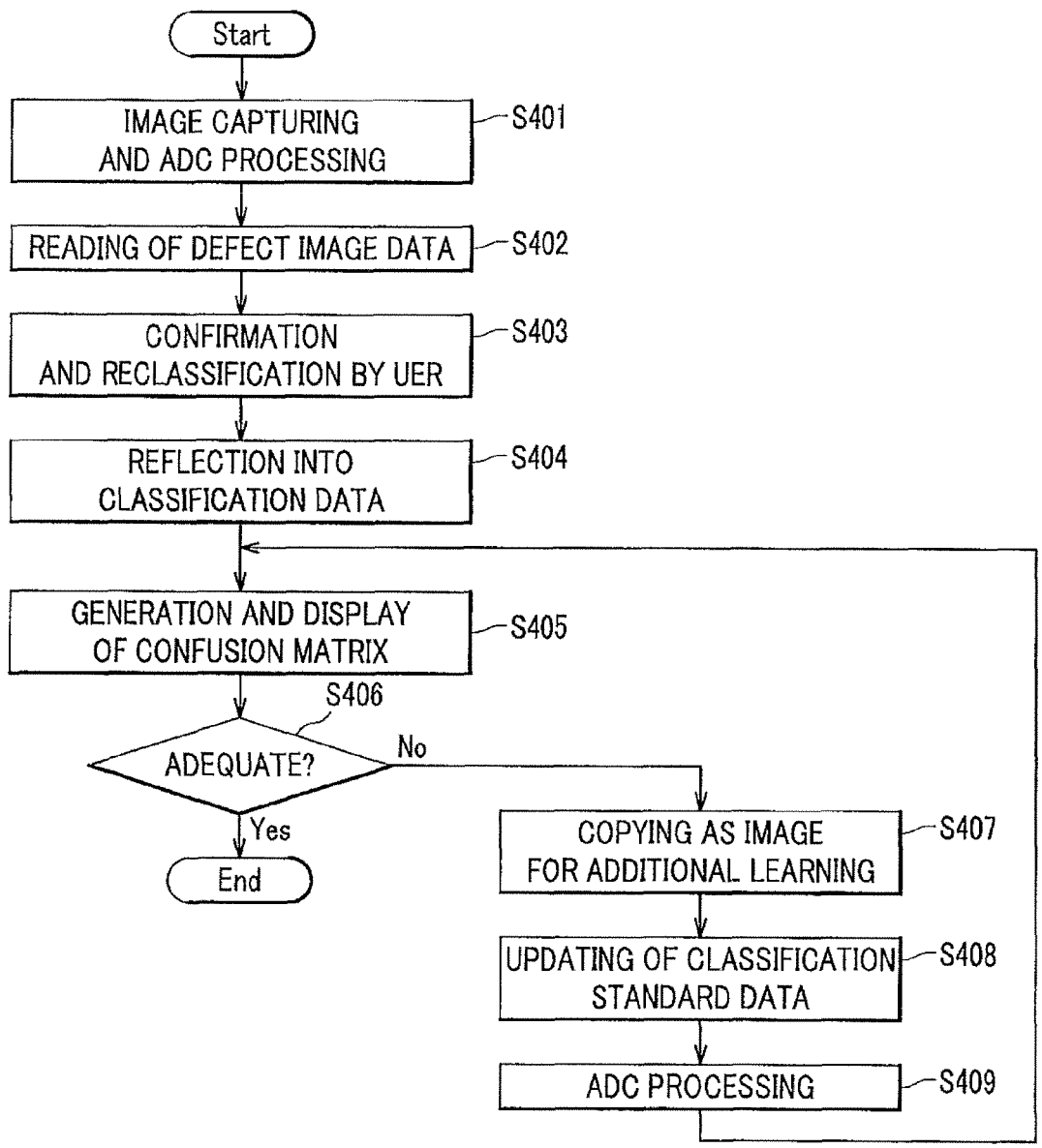
FIG. 11 is a flowchart showing the procedure of a process executed upon newly obtaining defect image data.

FIG. 11 is a flowchart showing the process executed when defect image data is obtained anew.

First, when the review device 1 captures new defect image data after the process in FIG. 6, the characteristic amount extraction section 114 automatically adjusts the defect recognition parameters, thereafter extracts characteristic amounts, and the automatic defect classification section 113 performs ADC processing of the captured defect image data (S401) and thereby classifies defect images. A result of ADC processing is registered in the classification data 122 shown in FIG. 4. Automatic adjustment of defect recognition parameters and extraction of characteristic amounts are similar to the processes in S203, S204 in FIG. 6, and description will be accordingly omitted.

Then, when an instruction of classification by the user is entered via the input section 13, the input processing section 112 reads the newly input defect image data from the defect image data group 123 in the storage section 12, based on the information on update date-and-time and the like (S402).

At this moment, the display processing section 111 also reads the classification data 122, in FIG. 4, and displays a result of classification by ADC in which a result of ADC processing and defect images are associated with each other on the display section 14. The user refers to the displayed classification result and confirms whether the classification has been correctly made by the ADC processing, and, if there are errors in classification, the user performs reclassification into appropriate categories (S403). The input processing section 112 reflects a result of the reclassification into the classification data 122 in FIG. 4 (S404). The order of reflection is similar to that in S206, in FIG. 6, except that the order "classification by user→classification by ADC" has changed to "classification by ADC→classification by user", and detailed description will be accordingly omitted.

Then, the display processing section 111 generates a confusion matrix 211a (FIG. 13), based on the classification data 122, and displays a check screen 500 (FIG. 13) including this confusion matrix 211a (S405). The procedure of generating the confusion matrix 211a, based on the classification data 122, is similar to the procedure described above with reference to FIG. 8, and detailed description will be accordingly omitted.

Then, the user determines whether or not the current classification result is appropriate, referring to the displayed check screen 500 (FIG. 13) (S406).

As a result of S406, if it is determined to be adequate (i.e., the classification result is appropriate.) (S406→Yes), then the process is terminated.

As a result of S406, if it is determined to be inadequate (i.e., the classification result is inappropriate.) (S406→No), then the display processing section 111 copies defect image data selected via the check screen 500 as image data for additional learning (S407).

Then, the display processing section 111 updates the classification standard data 121 (S408); the characteristic amount extraction section 114 performs automatic adjustment of the defect reorganization parameters and extraction of characteristic amounts; and the automatic defect classification section 113 thereafter performs ADC processing, based on the updated classification standard data 121 (S409). S407 and S408 will be described later.

Subsequently, the processing section 11 returns the process to S405.

The procedure of a check process will be described below, based on FIG. 12 and referring to FIGS. 3, and 13 to 15, as appropriate. The process shown in FIG. 12 corresponds to S405 to S408 in FIG. 11.

FIG. 12 is a flowchart showing the procedure of a check process according to the present embodiment.

Figure 13:
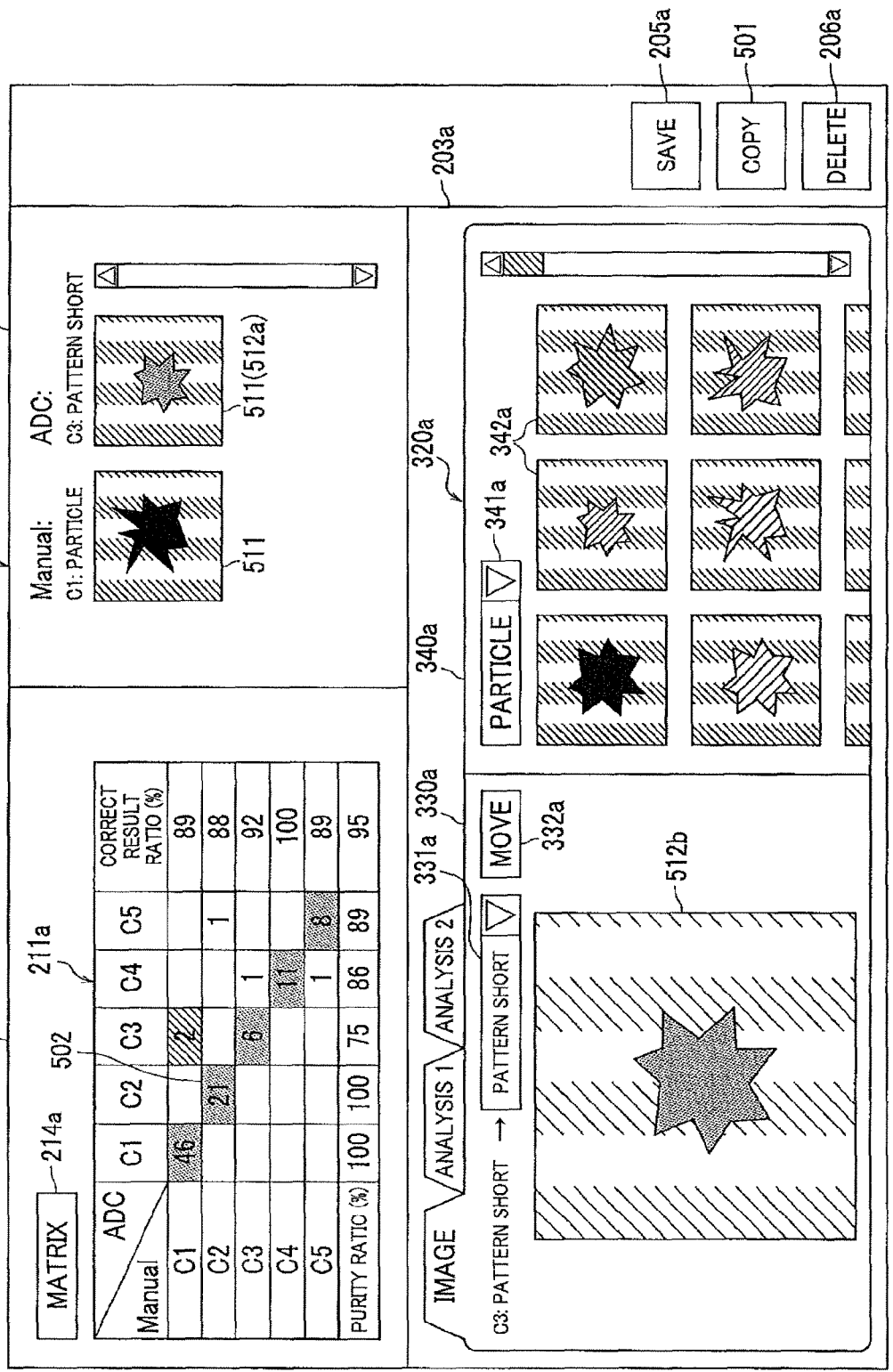
FIG. 13 is a diagram showing an example of a check screen (image comparison) in the present embodiment.
Figure 14:
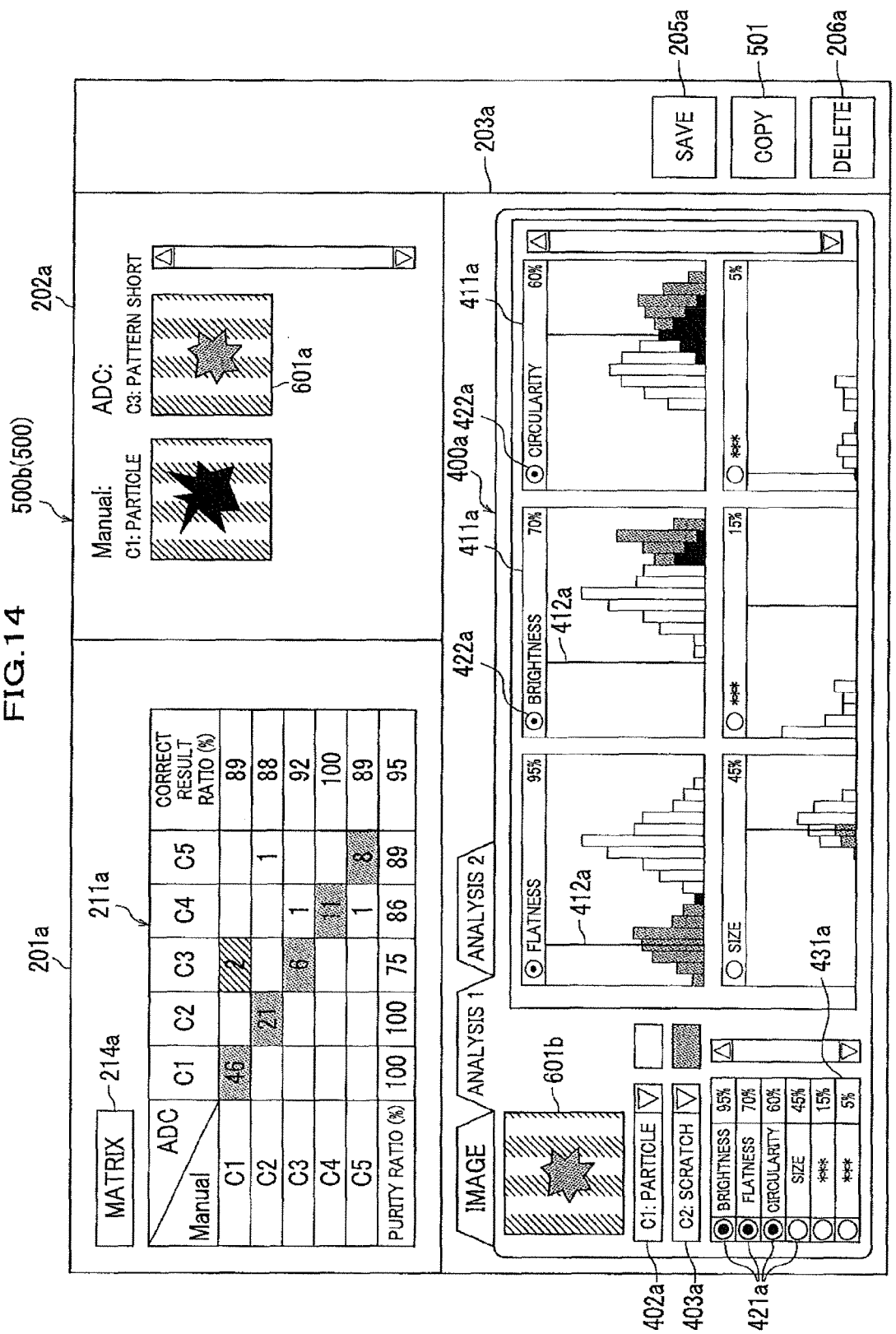
FIG. 14 is a diagram showing an example of a check screen (characteristic amount comparison) in the present embodiment.

First, the display processing section 111 displays a check screen 500a (500), shown in FIG. 13, and a check screen 500b (500), shown in FIG. 14, and performs an image comparison process/characteristic amount comparison process (S501). S501 is a process similar to the process shown in FIG. 6 except that classification data 122 is used instead of classification standard data 121, and detailed description will be accordingly omitted.

FIG. 13 is a diagram showing an example of a check screen (image comparison) according to the present embodiment.

In the check screen 500a (500), the symbols 201a, 202a, 203a, 205a, 206a, 211a, 214a, 320a, 330a, 331a, 332a, 340a, 341a, and 342a are similar to the symbols 201, 202, 203, 205, 206, 211, 214, 320, 330, 331, 332, 340, 341, and 342 in FIG. 9, except that the symbols in the check screen 500a (500) are created, based on classification data 122, while the symbols in FIG. 9 are created, based on classification standard data 121, and description will be accordingly omitted. Further, although "analysis tab" in FIG. 9 is replaced by "analysis 1 tab" in the check screen 500a (500), these functions are similar. A copy button 501 will be described later.

In the example in FIG. 13, when a cell 502 in the confusion matrix 211a created based on the classification data 122 is selected via the input section 13, the display processing section 111 displays corresponding defect images 511 in the defect image list display area 202a. One defect image 512a among the defect images 511 is copied by drag and drop into an object image display area 330a and displayed as a defect image 512b.

A move button 332a, in FIG. 13, is a button for moving the data of the selected defect image 512b to another category in the same classification data 122.

FIG. 14 is a diagram showing an example of a check screen (characteristic amount comparison) according to the present embodiment.

In the check screen 500b (500), the symbols 201a, 202a, 203a, 205a, 206a, 211a, 214a, 400a, 402a, 403a, 411a, 412a, 421a, 422a, and 431a are similar to the symbols 201, 202, 203, 205, 206, 211, 214, 400, 402, 403, 411, 412, 421, 422, and 431 in FIG. 10, except that the symbols in the check screen 500b (500) are created, based on classification data 122, while the symbols in FIG. 10 are created, based on classification standard data 121, and description will be accordingly omitted.

In the example in FIG. 14, one (symbol 601a) among defect images displayed in the defect image list display area 202a is copied by drag and drop into a characteristic amount display area 400a and displayed as a defect image 601b.

Returning to FIG. 12, subsequent to S501, the display processing section 111 determines whether or not "analysis 2 tab" in FIG. 13 or 14 has been selected and entered (whether or not selected) (S502).

As a result of S502, if "analysis 2 tab" has not been selected (S502→No), the display processing section 111 proceeds the process to S505.

Figure 15:
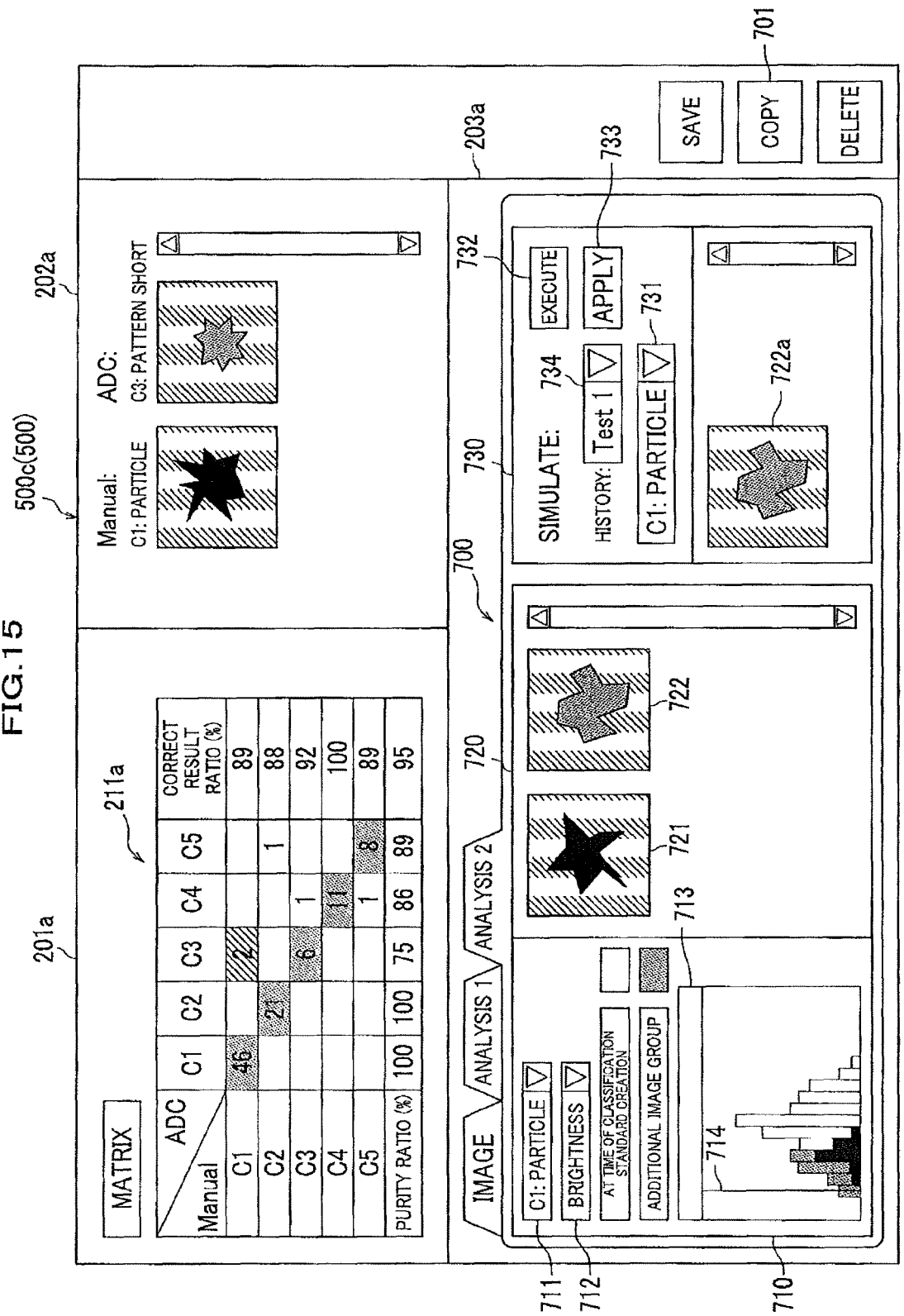
FIG. 15 is a diagram showing an example of a check screen (simulation) in accordance with the present embodiment.

As a result of S502, if "analysis 2 tab" has been selected (S502→Yes), the display processing section 111 displays a check screen 500c (500), shown in FIG. 15.

FIG. 15 is a diagram showing an example of a check screen (simulation) according to the present embodiment In FIG. 15, elements similar to those in FIGS. 13 and 14 are given with the same symbols, and description will be omitted.

In the check screen 500c (500), a simulate area 700 is displayed in the defect image confirmation area 203a. The simulate area 700 includes a characteristic amount display area 710, a defect image display area 720, and a simulate execution area 730.

The display processing section 111 determines whether or not a category has been selected via a category selection pull-down menu 711 in the characteristic amount display area 710 (S503 in FIG. 12). If not selected (S503→No), the display processing section 111 proceeds the process to S505 in FIG. 12.

If a category has been selected via the category selection pull-down menu 711 (S503→Yes) and further a characteristic amount type is selected via a characteristic amount type selection pull-down-menu 712, then the display processing section 111 generates a histogram representing characteristic amount distribution, based on the classification standard data 121 and the classification data 122, and displays the generated histogram in a characteristic amount distribution display area 713 (S504).

The histogram displayed in the characteristic amount distribution display area 713 is different from the histogram displayed in FIG. 10 or 14, and represents the characteristic amount distribution of the classification standard data 121 and the characteristic amount distribution of the newly added defect image data group 123, with respect to the same category and characteristic amount type.

In the example in FIG. 15, the histogram at the time of creation of the classification standard (namely the classification standard data 121) for the category "C1: particle" and the characteristic amount type "brightness" is displayed as a hollow histogram, and the histogram of the group of additional images (namely the classification data 122) is displayed as a hatched histogram. The portion where the two histograms are overlapped with each other is black solid.

The procedure of creating histograms is as follows. First, the display processing section 111 refers to the categories selected by user of the classification standard data 121 by using the category name selected via the category selection pull-down menu 711 as a key, and obtains all corresponding defect image data names. Then, the display processing section 111 refers to the characteristic amount type, in the standard characteristic amount data 124, selected via the characteristic amount type selection pull-down-menu 712, by using all the obtained defect image data names as a key, and counts the numbers of defect image data for the respective values of characteristic amounts. The display processing section 111 performs a similar process on the classification data 122.

By histograms created in this manner, the user can visually recognize the difference between the characteristic amount distribution of the classification standard data 121 and the characteristic amount distribution of the classification data 122. For example, from the characteristic amount distribution display area 713, regarding the category (the category classified by the user) of "C1: particle" and the characteristic amount type of "brightness", it is observed that the characteristic amount distribution of the group of additional images concentrate in lower values (the left side of the graph) compared with that at the time of creation of the classification standard (classification standard data 121). Therefore, it is found to be appropriate to supplement data having the lower values in the characteristic amount distribution to the classification standard data 121.

Then, if a bar 714 is moved via the input section 13, the display processing section 111 obtains defect image data of the value at which this bar 714 is located and displays the defect image data in the defect image display area 720. In the example in FIG. 15, as the bar 714 indicates the value at the leftmost side of the histogram, defect images 721, 722 with this value of brightness and of category "C1: particle" are displayed.

More specifically, upon reading the value of the characteristic amount indicated by the bar 714, the display processing section 111 searches the value of the characteristic amount type selected via the characteristic amount type selection pull-down-menu 712 in the characteristic amount data 125 in FIG. 5 by using the read value as a key, and obtains defect image data names having this value. The display processing section 111 refers to the user categories of the classification data 122 by using the obtained defect image date names as a key, and obtains image data names corresponding to the category selected via the category selection pull-down menu 711 from the obtained defect image data names. Then, the display processing section 111 obtains defect image data from the defect image data group 123, by using the obtained defect image data names as a key, and displays the obtained defect image data in the defect image display area 720. Incidentally, as an example of a default arrangement, the value at the leftmost of the histogram may be selected unless the user moves the bar 714.

When the characteristic amount distribution at the time of creating the classification standard (classification standard data 121) and the characteristic amount distribution of the group of the additional images (classification data 122) are superimposed with each other, the characteristic amount type selection pull-down-menu 712 may display the characteristic amount types in ascending order of lower agreement ratio (i.e., in descending order of higher separation degree).

Then, the display processing section 111 determines whether or not a defect image displayed in the defect image display area 720 has been dragged and dropped into the simulate execution area 730 via the input section 13, and thereby determines whether or not a defect image has been selected (S505 in FIG. 12).

As a result of S505, if a defect image has not been selected (S505→No), the display processing section 111 proceeds the process to S508 in FIG. 12.

As a result of 505, if a defect image has been selected (S505→Yes), the display processing section 111 displays the dragged and dropped defect image in the simulate execution area 730 in FIG. 15.

In the example in FIG. 15, among the defect images 721, 722 displayed in the defect image display area 720, the defect image 722 has been dragged and dropped (selected) and is displayed in the simulate execution area 730 as a defect image 722*a*, however, it is possible to select a plurality of defect images.

Then, the user selects as to which category (category by user in the classification standard data 121) the defect image 722*a* displayed in the simulate execution area 730 is to be moved, via a category selection pull-down menu 731, and the display processing section 111 thereafter determines whether or not an execution button 732 has been selected and thereby determines whether or not to execute simulation (S506 in FIG. 12).

As a result of S506, if simulation is not to be executed (S506→No), the display processing section 111 proceeds the process to S508.

As a result of S506, if simulation is to be executed (S506→Yes), the characteristic amount extraction section 114 performs simulation on what a generated confusion matrix 211*a* will be like if the defect image 722*a* displayed in the simulate execution area 730 is added to the classification standard data 121, and displays a result in the display section 14 (S507 in FIG. 12). More specifically, the automatic defect classification section 113 uses temporary classification standard data 121, to which the defect image 722*a* is added, to perform reclassification of the defect image data group 123 with the newly added defect image data; and thereby creates a temporary classification data 122. Then, the display processing section 111 generates a confusion matrix 211*a* from the temporary classification data 122 by a method similar to the above-described procedure, and then displays this confusion matrix 211*a* in the confusion matrix display area 201*a*, thereby updating the confusion matrix 211*a*.

At the moment of S507, the data of the defect image 722*a* has not actually been added to the classification standard data 121, and only simulation is performed on what a generated confusion matrix 211a will be like if the data of the defect image 722a is added to the classification standard data 121. As a result of simulation (defect image data to be added, category, confusion matrix 211a, temporary classification standard data 121, temporary classification data 122, etc.) may be held by the display processing section 111 in the storage section 12 as history. In this case, if the user selects a history via a history selection pull-down menu 734, then the display processing section 111 displays the state at that time (defect image data to be added, category, confusion matrix 211a, temporary classification standard data 121, temporary classification data 122, etc.) on the check screen 500.

Referring to the confusion matrix 211a updated as a result of the simulation, the user determines whether or not it is appropriate to add the defect image 722a displayed in the simulate execution area 730 to the classification standard data 121. If determined to be appropriate, a copy button 701 is selected and entered via the input section 13. That is, the display processing section 111 determines whether or not the copy button 701 has been selected and entered, and thereby determines whether or not to copy the defect image 722a to the classification standard data 121 (S508 in FIG. 12). The process in S508 corresponds to S406 in FIG. 11.

If determined not to copy (S508→No), the processing section 11 terminates the process.

If determined to copy (S508→Yes), the display processing section 111 copies the corresponding defect image 722a to the classification standard data 121 (S509 in FIG. 12). Actually, the display processing section 111 copies a defect image data name corresponding to the defect image 722a displayed in the simulate execution area 730 to the classification standard data 121. The process in S509 is corresponding to S407 in FIG. 11.

Subsequently, the display processing section 111 determines whether or not an application button 733 has been selected and entered, and thereby determines whether or not to apply copy (S510 in FIG. 12).

If determined not to apply copy (S510→No), the processing section 11 terminates the process. A case of not applying copy refers to a case that the application button 733 has not been selected and entered for a certain time after application of the copy button 701, a case that a delete button 206a has been selected and entered, a case that the check screen 500 has been closed, and other cases.

In a case of applying copy (S510→Yes), the display processing section 111 additionally registers the data name of the defect image 722a displayed in the simulate execution area 730 into the classification standard data 121, and updates the classification standard data 121 (fixes the classification standard data 121: S511 in FIG. 12).

Alternatively, by retrieving the history of simulation via the history selection pull-down menu 734 and selecting and entering the application button 733, a state corresponding to the history of simulation may be reflected and fixed into the classification standard data 121. Incidentally, the copy button 701 may be omitted, and the process in S508 may be omitted. In this case, if the application button 733 is selected and entered, then the defect image data name is copied into the classification standard data 121 and simultaneously subjected to applying processing.

In the present invention, a histogram showing characteristic amount distribution is displayed, however, the invention is mot limited thereto. For example, it is also possible to display characteristic amount distribution by a scatter diagram or the like.

According to the present invention, the classification standard data 121 used for ADC can be created or updated by comparing respective defect images, comparing characteristic amount distributions, moving image data names in the classification standard data 121 as a result of these comparisons, and copying defect image data names in classification data 122 into the classification standard data 121. As a result, it is possible to prevent the classification performance of a classification standard from being reduced due to inappropriate learning, and improve the classification accuracy of ADC. Furthermore, a user can effectively determine appropriateness/inappropriateness of classification of defect images because it is possible to effectively display and modify characteristic amounts between categories to be objects of classification, such as displaying defect images and characteristic amount distributions. That is, as a device for automatic classification of detects, it is possible to improve the operability in creating a classification standard, improve the user-friendliness, and more quickly and accurately create and adjust a classification standard. Accordingly, it is possible to more accurately feed back the occurrence state of detect type to which attention is paid, to a line, and thereby improve the yield ratio of the line.

In addition, even when a defect of a type which is not registered in a classification standard is detected, flexible measures can be taken.

REFERENCE NUMERALS 1 review device (image classification device)
1a optical review device
1b SEM review device.
11 processing section
12 storage section
13 input section
14 display section
15 transmitting/receiving section
111 display processing section
112 input processing section
113 automatic defect classification section
114 characteristic amount extraction section
115 data obtaining section
121 classification standard data
122 classification data
123 defect image data group
124 standard characteristic amount data
125 characteristic amount data
200, 200a, 200b, 200c self-check screen
211, 211a confusion matrix (association information between categories)
Z semiconductor wafer manufacturing system

The invention claimed is:

1. A method for updating an image classification standard by an image classification device automatically classifying image data, comprising the steps of:
   storing in a storage section of the image classification device:
   classification standard data which includes information on image data used as a standard for automatically classifying the image data, and
   classification data which includes information on image data of newly input image data automatically classified using the classification standard data; and
   updating the classification standard data by adding information on image data selected by a user from the image data included in the classification data into the classification standard data when an instruction is input via an input section of the image classification device to add the information on image data selected by the user from the image data included in the classification data into the classification standard data.

2. The method for updating an image classification standard according to claim 1, further comprising the step, carried out by the image classification device, of displaying an image corresponding to the information on image data in the classification standard data and an image corresponding to the information on image data in the classification data, in the same window.

3. The method for updating an image classification standard according to claim 1, further comprising the steps, carried out by the image classification device, of: storing in the storage section:

standard characteristic amount data that is data of characteristic amounts related to the information on image data in the classification standard data, and characteristic amount data that is data of characteristic amounts related to the information on image data in the classification data; and displaying distribution of characteristic amounts in the standard characteristic amount data and distribution of characteristic amounts in the characteristic amount data, in the same window.

4. The method for updating an image classification standard according to claim 1, the method further comprising the steps, carried out by the image classification device, of:

simulating reclassification of the information on the newly input image data, by using the classification standard data which the information on the image data selected by the user has been added; and displaying the result of the simulation on a display section of the image classification device.

5. The method for updating an image classification standard according to claim 1, the method further comprising the steps, carried out by the image classification device, of:

adding information on image data newly input into the classification data into categories into which information on image data is classified by a user and categories into which information on image data is automatically classified using the classification standard data;

generating association information between categories in which image data belonging to each of the categories classified by the user in the classification data is matched with image data belonging to each of the categories automatically classified by the image classification device in the classification data; and displaying the generated association information between categories on a display section of the image classification device.

6. The method for updating an image classification standard according to claim 5, the method further comprising the steps, carried out by the image classification device, of:

displaying the association information between categories on the display section in a matrix having a plurality of cells, each cell showing a number of image data in the association information between categories, displaying image data on the display section when one of the cells showing the corresponding number of the image data in the association information between categories is selected.

7. The method for updating an image classification standard according to claim 1, wherein the image data is a defect image of a semiconductor wafer.

8. A non-transitory computer-readable medium storing a program for executing, on a computer, the method for updating an image classification standard according to claim 1.

9. A method for updating an image classification standard by an image classification device automatically classifying image data, comprising the steps of:

storing in a storage section of the image classification device classification standard data which includes information on image data used as a standard for automatically classifying image data, and the image data classified in respective categories; and updating the classification standard data by moving image data selected by a user from the image data in the classification standard data, from a category in which the image data selected by the user is classified, to a different category in the classification standard data, when an instruction is inputted via an input section of the image classification device to move the image data selected by the user, from the category in which the image data selected by the user is classified, to the different category in the classification standard data.

10. The method for updating an image classification standard according to claim 9, further comprising the step, carried out by the image classification device, of displaying image data in the different category in the classification standard data in the same window with the image data selected by the user on a display section of the image classification device.

11. The method for updating an image classification standard according to claim 9, further comprising the steps, carried out by the image classification device, of:

storing in each of the categories in the storage section standard characteristic amount data that is data of characteristic amounts of the image data in the classification standard data; and displaying distributions of the characteristic amounts of two categories selected by a user from the standard characteristic amount data in distinguishable figure in the same graph on a display section of the image classification device.

12. The method for updating an image classification standard according to claim 9, further comprising the steps, carried out by the image classification device, of:

storing the image data in the classification standard data in each of categories into which the image data is classified by a user and each of categories into which the image data is automatically classified using the classification standard data, generating association information between categories in which image data belonging to each of the categories classified by the user in the classification standard data is matched with image data belonging to each of the categories automatically classified by the image classification device in the classification standard data; and displaying the generated association information between categories on a display section of the image classification device.

13. The method for updating an image classification standard according to claim 12, further comprising the steps, carried out by the image classification device, of:

displaying the association information between categories on the display section in a matrix having a plurality of cells, each cell showing a number of image data in the association information between categories;

selecting one of the cells showing a number of image data in the association information between categories; and displaying the corresponding image data on the display section.

14. The method for updating an image classification standard according to claim 9, wherein the image data are defect images of semiconductor wafers.

15. An image classification device automatically classifying image data, comprising:

a storage section that stores classification standard data which includes information on image data used as a standard for automatically classifying the image data, and classification data which includes information on image data of newly input image data automatically classified using the classification standard data; and a processing section that updates the classification standard data by adding information on image data selected by a user from image data included in the classification data into the classification standard data when an instruction is input via an input section of the image classification device to add the information on the image data selected by the user into the classification standard data.

16. An image classification device automatically classifying image data, comprising:

a storage section that stores classification standard data which includes image data being classified in respective categories and information on the image data used as a standard for automatically classifying image data; and a processing section that updates the classification standard data by moving image data selected by a user from the image data in the classification standard data, from a category in which the image data selected by the user is classified to a different category in the classification standard data when an instruction is input via an input section of the image classification device to move the image data selected by the user, from the category in which the image data selected by the user is classified to the different category.

17. The image classification device according to claim 16, wherein the image data is stored in the classification standard data in each of categories into which the image data is classified by a user and each of categories into which the image data is automatically classified using the classification standard data; and processing section generates association information between categories in which image data belonging to each of the categories classified by a user in the classification standard data is matched with image data belonging to each of the categories automatically classified by the image classification device in the classification standard data, and displays the generated association information between categories on a display section of the image classification device.

18. The image classification device according to claim 17, wherein the association information between categories is displayed on the display section in a matrix having a plurality of cells, each cell showing a number of image data in the association information between categories; and the processing section displays image data in the association information between categories on the display section when one of the cells corresponding to the image data.

* * * * *